(12) United States Patent
Klug et al.

(10) Patent No.: US 9,949,909 B2
(45) Date of Patent: Apr. 24, 2018

(54) USE OF SPECIAL N-ALKYL-N-ACYLGLUCAMINES FOR CONDITIONING HAIR IN HAIR WASHING AGENTS

(71) Applicant: Clariant International Ltd., Muttenz (CH)

(72) Inventors: Peter Klug, Grossostheim (DE); Carina Mildner, Frankfurt am Main (DE); Henrike Neuhoff, Wiesbaden (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 14/899,835

(22) PCT Filed: Jun. 25, 2014

(86) PCT No.: PCT/EP2014/001723
§ 371 (c)(1),
(2) Date: Dec. 18, 2015

(87) PCT Pub. No.: WO2014/206555
PCT Pub. Date: Dec. 31, 2014

(65) Prior Publication Data
US 2016/0143828 A1    May 26, 2016

(30) Foreign Application Priority Data

Jun. 28, 2013 (DE) .................. 10 2013 212 750
Nov. 29, 2013 (DE) .................. 10 2013 224 561

(51) Int. Cl.
| | | |
|---|---|---|
| *A61K 8/42* | (2006.01) | |
| *A61K 8/41* | (2006.01) | |
| *A61Q 5/02* | (2006.01) | |
| *A61Q 5/12* | (2006.01) | |
| *A61K 8/46* | (2006.01) | |
| *A61Q 5/00* | (2006.01) | |
| *A61Q 17/04* | (2006.01) | |

(52) U.S. Cl.
CPC .................. *A61K 8/42* (2013.01); *A61K 8/41* (2013.01); *A61K 8/463* (2013.01); *A61Q 5/006* (2013.01); *A61Q 5/008* (2013.01); *A61Q 5/02* (2013.01); *A61Q 5/12* (2013.01); *A61K 2800/596* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 5,009,814 A | 4/1991 | Kelkenberg et al. | |
| 2001/0023298 A1 | 9/2001 | Weinelt | |
| 2009/0023622 A1 | 1/2009 | Leidreiter et al. | |
| 2011/0150786 A1* | 6/2011 | Desenne ................. | A61K 8/31 424/47 |
| 2015/0125415 A1 | 5/2015 | Klug et al. | |
| 2015/0126424 A1 | 5/2015 | Klug et al. | |
| 2015/0126616 A1 | 5/2015 | Klug et al. | |
| 2015/0133560 A1 | 5/2015 | Klug et al. | |
| 2015/0140048 A1 | 5/2015 | Klug et al. | |
| 2015/0141466 A1 | 5/2015 | Klug et al. | |
| 2015/0141508 A1 | 5/2015 | Klug et al. | |
| 2015/0150767 A1 | 6/2015 | Klug et al. | |
| 2015/0164755 A1 | 6/2015 | Klug et al. | |
| 2015/0164756 A1 | 6/2015 | Klug et al. | |
| 2015/0320037 A1 | 11/2015 | Wacker | |
| 2016/0074310 A1 | 3/2016 | Klug et al. | |
| 2016/0136072 A1 | 5/2016 | Klug et al. | |
| 2016/0243014 A1 | 8/2016 | Dahms et al. | |

(Continued)

FOREIGN PATENT DOCUMENTS

| | | |
|---|---|---|
| DE | 4435383 | 11/1995 |
| DE | 19507531 | 9/1996 |

(Continued)

OTHER PUBLICATIONS

International Search Report for PCT/EP2014/001723, dated Jan. 5, 2015.
International Preliminary Report on Patentability for PCT/EP2014/001723, dated Jun. 8, 2015.
English Abstract for EP 1 043 017, Oct. 11, 2000.
English Abstract for DE 4435383, Nov. 9, 1995.
English Abstract for DE 19507531, Sep. 12, 1996.

*Primary Examiner* — Susan T Tran

(74) *Attorney, Agent, or Firm* — Tod Waldrop

(57) ABSTRACT

The invention relates to N-alkyl-N-acylglucamines of formula (I), which exhibit in hair-washing agents comprising an aqueous surfactant system with at least one anionic surfactant, a hair-conditioning effect, wherein, in formula (I), Ra is a linear or branched, saturated or unsaturated $C_5$-$C_{21}$ alkyl radical and Rb represents a $C_1$-$C_4$ alkyl radical, and wherein the N-alkyl-N-acylglucamines (I) contain at least 8 wt. %, based on the total amount of N-alkyl-N-acylglucamines (I), of compounds with a saturated $C_{16}$-, $C_{18}$- or a mono- or polyunsaturated $C_{18}$ fatty acid radical Ra—CO—.

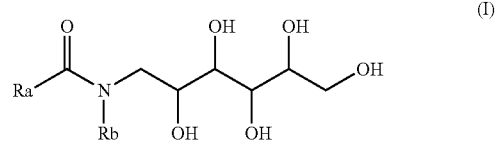

(I)

17 Claims, No Drawings

(56) References Cited

U.S. PATENT DOCUMENTS

| | | |
|---|---|---|
| 2016/0272666 A1 | 9/2016 | Klug et al. |
| 2016/0361243 A1 | 12/2016 | Klug et al. |
| 2017/0000710 A1 | 1/2017 | Klug et al. |
| 2017/0002297 A1 | 1/2017 | Klug et al. |
| 2017/0044434 A1 | 2/2017 | Baur et al. |
| 2017/0055524 A1 | 3/2017 | Baur et al. |
| 2017/0071199 A1 | 3/2017 | Baur et al. |
| 2017/0101606 A1 | 4/2017 | Klug et al. |
| 2017/0218293 A1 | 8/2017 | Klug et al. |
| 2017/0265477 A1 | 9/2017 | Baur et al. |
| 2017/0292062 A1 | 10/2017 | Wylde et al. |
| 2017/0305838 A1 | 10/2017 | Appel et al. |

FOREIGN PATENT DOCUMENTS

| | | |
|---|---|---|
| DE | 202013011412 | 3/2014 |
| DE | 202013011413 | 3/2014 |
| EP | 0 285 768 | 10/1988 |
| EP | 0 550 637 | 7/1993 |
| EP | 1 043 017 | 10/2000 |
| EP | 1 110 944 | 6/2001 |
| WO | WO 2013178668 | 12/2013 |
| WO | WO 2013178670 | 12/2013 |
| WO | WO 2013178671 | 12/2013 |
| WO | WO 2013178679 | 12/2013 |
| WO | WO 2013178697 | 12/2013 |
| WO | WO 2013178701 | 12/2013 |
| WO | WO 2014170025 | 10/2014 |

\* cited by examiner

USE OF SPECIAL N-ALKYL-N-ACYLGLUCAMINES FOR CONDITIONING HAIR IN HAIR WASHING AGENTS

The invention relates to the use of specific N-alkyl-N-acylglucamines for hair conditioning (haircare) in hairwash compositions.

Cosmetic hairwash compositions (shampoos) are subject to exacting requirements. They are to exhibit a good appearance, be toxicologically and ecotoxicologically unobjectionable, to provide excellent cleansing, while nevertheless generating a pleasant sensation on the hair.

The surfactant systems included in such compositions are required to fulfill a dual function. On the one hand, there is to be an adequate cleansing effect, which often, however, turns into a dull sensation on skin and hair if degreasing is too strong. On the other hand, following use, the hair is to have a cared-for sensation and, correspondingly, to exhibit great ease of combing as well.

These effects are normally achieved by adding additional hair-conditioning agents to the surfactant system employed for cleansing. These additional agents may be, for example, cationic surfactants (hydroxyethyl quats) or cationic polymers (polyquaternium-7, polyquaternium-10, cationic guar derivatives, chitosan derivatives). Furthermore, fatty acid esters (glyceryl oleate) or ethoxylated fatty acid esters (PEG-7 glyceryl cocoate) are used for this purpose. All of these substances, however, have disadvantages in their use. The cationic components in particular are of only limited compatibility, owing to their cationic nature, with the commonly employed surfactant systems or other components, such as opacifiers, for example.

It has now been found that certain N-alkyl-N-acylglucamines are suitable for use in commonly employed surfactant systems and at the same time also exhibit hair-conditioning activities. It was surprising that in this way a surfactant is able to take on the functions of customarily additional additives used in hairwash compositions.

EP-A 1 043 017 (DE 199 16 090) describes N-acyl-N-alkylglucamides for use as skincare compositions, in particular. No effects at all in relation to hair conditioning are described in this case, however.

A subject of the invention is therefore the use of N-alkyl-N-acylglucamines of the formula (I) in hairwash compositions, in particular as a hair-conditioning component, which have an aqueous surfactant system comprising at least one anionic surfactant,

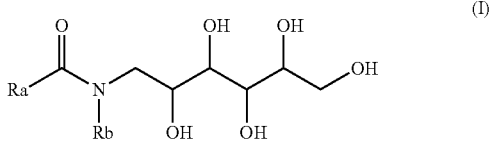

(I)

where in the formula (I)

Ra is a linear or branched, saturated or unsaturated $C_5$-$C_{21}$ alkyl radical, preferably $C_{11}$-$C_{17}$ alkyl radical, and Rb is a $C_1$-$C_4$ alkyl radical, preferably methyl, and the N-alkyl-N-acylglucamines (I) comprising at least 8 wt %, based on the total amount of N-alkyl-N-acylglucamines (I), of compounds having a saturated $C_{16}$, $C_{18}$, or singly or multiply unsaturated $C_{18}$ fatty acid radical Ra—CO—.

A further subject of the invention is a hairwash composition comprising (a) one or more N-methyl-N-acylglucamines (I) containing at least 8 wt %, based on the total amount of N-alkyl-N-acylglucamines (I), of compounds having a saturated $C_{16}$, $C_{18}$, or singly or multiply unsaturated $C_{18}$ fatty acid radical Ra—CO—, as component (A),
(b) one or more anionic surfactants from the group of the alkyl ether sulfates and alkyl sulfates, as component (B),
(c) optionally betaine surfactants as component (C),
(d) optionally further surfactants as component (D),
(e) one or more refatting agents as component (E),
(f) water as component (F), and
(g) optionally further additives, such as preservatives, fragrances, and dyes, as component (G).

Also subject of the invention is a method for hair cleansing by contacting the hair with a hairwash composition comprising the inventive N-alkyl-N-acylglucamines (I) as hair-conditioning components.

Surfactant systems comprising N-alkyl-N-acylglucamines (I) of the invention produce hair conditioning of a kind which may reduce or obviate the addition of further additives such as fatty acid esters, ethoxylated fatty acid esters, or cationic substances and so contributes to a simplification of the overall composition.

The N-alkyl-N-acylglucamines (I) used themselves have a hair-conditioning activity. Preference is therefore given to the use of the N-alkyl-N-acylglucamines (I) as hair-conditioning components in hairwash compositions.

The N-alkyl-N-acylglucamines (I) used in accordance with the invention, also known as N-alkyl-N-1-deoxysorbityl-fatty acid amides, contain at least 8, preferably at least 10, more preferably at least 15, very preferably at least 30, and especially preferably at least 60 wt % of N-alkyl-N-acylglucamines (I) having a saturated $C_{16}$, $C_{18}$ or a singly or multiply unsaturated $C_{18}$ acyl radical CO—Ra.

Preferred N-alkyl-N-acylglucamines (I) are those for which the radical CO—Ra derives from lauric acid, palmitic acid, stearic acid, oleic acid, linoleic acid, or linolenic acid. Especially preferred are N-methyl-N-acylglucamines of the formula (I) where the acyl radical CO—Ra derives from lauric acid, palmitic acid, oleic acid, linoleic acid, or linolenic acid.

Also preferred are N-alkyl-N-acylglucamines (I) which contain at least 8 wt %, preferably at least 15 wt %, of N-alkyl-N-acylglucamines (I) having a singly or multiply unsaturated $C_{18}$ fatty acid radical. Preference extends to N-alkyl-N-acylglucamines (I) which contain at least 8 wt % of N-alkyl-N-acylglucamines (I) having a multiply unsaturated $C_{18}$ fatty acid radical.

Where the N-alkyl-N-acylglucamines (I) used in accordance with the invention contain both unsaturated long-chain and medium-chain fatty acid radicals (C12), the resulting surfactant systems exhibit an outstanding combination of water solubility, cleansing performance, foam formation, and conditioning properties. Fatty acid mixtures of this kind are possessed for example by natural palm kernel oil and coconut oil.

Also preferred, accordingly, are embodiments wherein the N-alkyl-N-acylglucamines (I) contain at least 8 wt % of N-alkyl-N-acylglucamines (I) having a singly or multiply unsaturated $C_{18}$ fatty acid radical and at least 30 wt % having a saturated $C_{12}$ fatty acid radical.

The N-methyl-N-acylglucamines used as hair-conditioning agents in accordance with the invention preferably include only small fractions of N-methyl-N-acylglucamines containing $C_6$-$C_{10}$ acyl groups and derived from medium fatty acids. The fraction of such medium-length fatty acids is preferably not more than 15, more preferably 10, more particularly 5, wt %.

The N-methyl-N-acylglucamines (I) may be prepared, as described in EP-A 0 550 637 B1 and EP-A 0 285 768, by reaction of the corresponding fatty acid esters or fatty acid ester mixtures with N-methylglucamine in the presence of a solvent possessing hydroxyl groups or alkoxy groups. Examples of suitable solvents are $C_1$-$C_4$ monoalcohols, ethylene glycol, propylene glycol, glycerol, and alkoxylated alcohols. Preference is given to 1,2-propylene glycol. As likewise described in EP 0 550 637 A1, N-methylglucamine may be obtained by a reductive amination of glucose with methylamine. Suitable fatty acid esters reacted with the N-methylglucamines to give glucamides of the invention are generally the methyl esters, which are obtained by transesterification from natural fats and oils, the triglycerides for example.

Unsaturated $C_{18}$ acyl groups are understood in the sense of the invention to be fatty acid radicals having one or more double bonds. Preference in this context is given to radicals deriving from oleic acid, from linoleic acid, and from linolenic acid.

The aqueous surfactant systems used in accordance with the invention comprise one or more anionic surfactants, preferably from the group of the alkyl sulfates and alkyl ether sulfates, very preferably in combination with betaines.

In a further embodiment, the surfactant systems comprise fatty acid alkanolamides as well as alkyl ether sulfates and/or alkyl sulfates.

Preferred alkyl sulfates are the $C_8$-$C_{20}$ alkyl sulfates, more particularly the linear $C_8$-$C_{20}$ alkyl sulfates in the form of their sodium, potassium, or ammonium salts. Examples of alkyl sulfates are lauryl sulfate, cocoalkyl sulfate, and tallowalkyl sulfate. Lauryl sulfate is particularly preferred.

Preferred alkyl ether sulfates are the $C_8$-$C_{20}$ alkyl ether sulfates, more preferably the linear $C_8$-$C_{20}$ alkyl ether sulfates, more particularly the alkyl glycol ether sulfates derived from the ethoxylated fatty alcohols, in the form of their sodium, potassium, or ammonium salts. Examples of alkyl ether sulfates are lauryl ether sulfate, cocoalkyl ether sulfate, and tallowalkyl ether sulfate. Examples of glycol ether sulfates are lauryl triethylene glycol ether sulfate, cocoalkyl triethylene glycol ether sulfate, and tallowalkyl-hexaethylene glycol ether sulfate. Particular preference is given to lauryl glycol ether sulfate, as for example lauryldiethylene glycol ether sulfate or lauryltriethylene glycol ether sulfate, especially in the form of the sodium salts.

In a further preferred embodiment of the invention, the surfactant systems comprise one or more N-acylamino acid surfactants as anionic surfactants. In one preferred embodiment, the amino acid radical of such N-acyl-amino acid surfactants is selected from the group consisting of proteinogenic amino acids, their N-alkylated derivatives, or mixtures thereof.

Particularly preferred as N-acyl-amino acid surfactants are acylglycinates, acylalaninates, acylaspartates, acylglutamates, acylsarcosinates, or mixtures thereof. Especially preferred are the N-acyl-amino acid surfactants selected from the group consisting of acylglycinate, acylaspartate, acylglutamate, acylsarcosinate, and mixtures thereof.

With particular preference the N-acylamino acid surfactants consist of at least one $C_8$-$C_{22}$-acylated amino acid, more particularly the N-alkylated derivatives thereof. Preferred are the corresponding lauroyl or cocoyl derivatives of the amino acids.

Especially preferred accordingly are sodium cocoylglycinate, potassium cocoylglycinate, sodium lauroylglycinate, potassium lauroylglycinate, sodium cocoylglutamate, sodium lauroylglutamate, sodium cococylaspartate, sodium lauroylaspartate, and sodium lauroylsarcosinate.

The aqueous surfactant solutions preferably comprise a betaine surfactant as well as the at least one anionic surfactant.

Betaine surfactants include within the same molecule a cationic group, especially an ammonium group, and an anionic group, which may be a carboxylate group, sulfate group, or sulfonate group. Suitable betaines are alkylbetaines such as cocobetaine or fatty acid alkylamidopropylbetaines, as for example cocoacylamidopropyldimethylbetaine, $C_{12}$-$C_{18}$ dimethylaminohexanoates, or $C_{10}$-$C_{18}$ acylamidopropanedimethylbetaines.

In one preferred embodiment of the invention, the aqueous surfactant systems comprise one or more amidopropylbetaines of the formula (II),

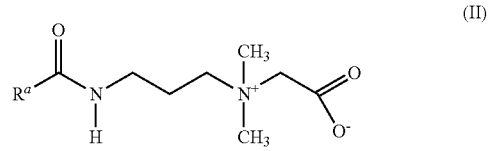

(II)

in which $R^a$ is a linear or branched saturated $C_7$-$C_{21}$ alkyl group or a linear or branched singly or multiply unsaturated $C_7$-$C_{21}$ alkenyl group.

In a further preferred embodiment of the invention, the surfactant systems comprise one or more betaines of the formula (III),

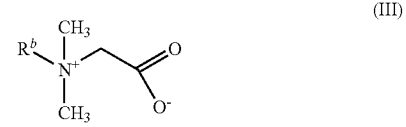

(III)

in which $R^b$ is a linear or branched saturated $C_8$-$C_{22}$ alkyl group or a linear or branched singly or multiply unsaturated $C_8$-$C_{22}$ alkenyl group.

In a further preferred embodiment of the invention, the surfactant systems comprise one or more sulfobetaines of the formula (IV),

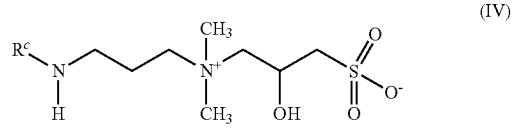

(IV)

in which $R^c$ is a linear or branched saturated $C_8$-$C_{22}$ alkyl group or a linear or branched singly or multiply unsaturated $C_8$-$C_{22}$ alkenyl group.

With particular preference, besides one or more alkyl sulfates and/or alkyl ether sulfates, the surfactant systems comprise one or more betaine surfactants selected from the group of the compounds consisting of the amidopropylbetaines of the formula (II), the betaines of the formula (III), and the sulfobetaines of the formula (IV).

In an especially preferred embodiment of the invention, the surfactant solutions comprise one or more betaine surfactants selected from the amidopropylbetaines of the formula (II).

In a further especially preferred embodiment of the invention, the surfactant solutions comprise one or more betaine surfactants selected from the betaines of the formula (III).

In a further especially preferred embodiment of the invention, the surfactant solutions comprise one or more betaine surfactants selected from the sulfobetaines of the formula (IV).

The radical $R^a$ in the one or more amidopropylbetaines of the formula (II) is preferably a linear or branched saturated $C_7$-$C_{17}$ alkyl group. Among the linear and branched saturated alkyl groups $R^a$, the linear saturated alkyl groups are preferred.

With particular preference the amidopropylbetaines of the formula (II) are cocoamidopropylbetaines.

The radical $R^b$ in the one or more betaines of the formula (II) is preferably a linear or branched saturated $C_8$-$C_{18}$ alkyl group and more preferably a linear or branched saturated $C_{12}$-$C_{18}$ alkyl group. Among the linear and branched saturated alkyl groups $R^b$, the linear saturated alkyl groups are preferred.

The radical $R^c$ in the one or more sulfobetaines of the formula (IV) is preferably a linear or branched saturated $C_8$-$C_{18}$ alkyl group and more preferably a linear or branched saturated $C_{12}$-$C_{18}$ alkyl group. Among the linear and branched saturated alkyl groups $R^c$, the linear saturated alkyl groups are preferred.

The aqueous surfactant solutions more preferably comprise amidopropylbetaines of the formula (I) and/or alkylbetaines of the formula (II).

Optional further surfactants (D) may be cationic, nonionic, or amphoteric surfactants.

Suitable cationic surfactants are substituted or unsubstituted, straight-chain or branched, quaternary ammonium salts of the type $R^1N(CH_3)_3X$, $R^1R^2N(CH_3)_2X$, $R^1R^2R^3N(CH_3)X$ or $R^1R^2R^3R^4NX$. The radicals $R^1$, $R^2$, $R^3$ and $R^4$ may preferably, independently of one another, be unsubstituted alkyl having a chain length between 8 and 24 carbon atoms, more particularly between 10 and 18 carbon atoms, hydroxyalkyl having 1 to 4 carbon atoms, phenyl, $C_2$ to $C_{18}$ alkenyl, $C_7$ to $C_{24}$ aralalkyl, $(C_2H_4O)_xH$, where x is from 1 to 3, alkyl radicals containing one or more ester groups, or cyclic quaternary ammonium salts. X is a suitable anion. Preferred are $(C_8$-$C_{22})$-alkyltrimethylammonium chloride or bromide, particularly preferred are cetyltrimethylammonium chloride or bromide, di-$(C_8$-$C_{22})$-alkyldimethylammonium chloride or bromide, $(C_8$-$C_{22})$-alkyldimethylbenzylammonium chloride or bromide, $(C_8$-$C_{22})$-alkyldimethylhydroxyethylammonium chloride, phosphate, sulfate, lactate, particularly preferred are distearyldimethylammonium chloride, di($C_8$-$C_{22}$)-alkylamidopropyltrimethylammonium chloride and methosulfate.

The amount of the cationic surfactants in the compositions of the invention may be up to 10 wt %, based on the overall weight of the completed compositions.

The following compounds can be considered as nonionic surfactants for example:

Polyethylene oxide, polypropylene oxide, and polybutylene oxide condensates of alkylphenols. These compounds comprise the condensation products of alkylphenols having a $C_6$ to $C_{20}$ alkyl group, which may be either linear or branched, with alkene oxides. These surfactants are referred to as alkylphenol alkoxylates, e.g., alkylphenol ethoxylates.

Condensation products of aliphatic alcohols with 1 to 25 mol of ethylene oxide. The alkyl or alkenyl chain of the aliphatic alcohols may be linear or branched, primary or secondary, and contains generally 8 to 22 carbon atoms. Particular preference is given to the condensation products of $C_{10}$ to $C_{20}$ alcohols with 2 to 18 mol of ethylene oxide per mole of alcohol. The alcohol ethoxylates may have a narrow ("narrow range ethoxylates") or a broad homolog distribution of the ethylene oxide ("broad range ethoxylates"). Examples of commercially available nonionic surfactants of this type are Tergitol® 15-S-9 (condensation product of a linear secondary $C_{11}$-$C_{15}$ alcohol with 9 mol of ethylene oxide), Tergitol® 24-L-NMW (condensation product of a linear primary $C_{12}$-$C_{14}$ alcohol with 6 mol of ethylene oxide, having narrow molar weight distribution). This product class likewise includes the Genapol® brands from Clariant.

Condensation products of ethylene oxide with a hydrophobic basis, formed by condensation of propylene oxide with propylene glycol. The hydrophobic moiety of these compounds preferably has a molecular weight between 1500 and 1800. The addition of ethylene oxide onto this hydrophobic moiety leads to an improvement in the water solubility. The product is liquid up to a polyoxyethylene content of about 50% of the total weight of the condensation product, which corresponds to a condensation with up to about 40 mol of ethylene oxide. Commercially available examples of this product class are the Pluronic® brands from BASF and the Genapol® PF brands from Clariant.

Condensation products of ethylene oxide with a reaction product of propylene oxide and ethylenediamine. The hydrophobic unit of these compounds consists of the reaction product of ethylenediamine with excess propylene oxide and generally has a molecular weight of 2500 to 3000. Ethylene oxide is added onto this hydrophobic unit up to a content of 40 to 80 wt % of polyoxyethylene and a molecular weight of 5000 to 11 000. Commercially available examples of this compound class are the Tetronic® brands from BASF and the Genapol® PN brands from Clariant.

Further suitable nonionic surfactants are alkyl- and alkenyl-oligoglycosides and fatty acid polyglycol esters or fatty amine polyglycol esters each having 8 to 20 and preferably 12 to 18 carbon atoms in the fatty alkyl radical, alkyl-oligoglycosides, alkenyl-oligoglycosides, and fatty acid N-alkylglucamides.

The amount of the nonionic surfactants in the compositions of the invention may be up to 10 wt %, based on the overall weight of the completed compositions.

In addition, the compositions of the invention may comprise amphoteric surfactants. These may be described as derivatives of long-chain secondary or tertiary amines which possess an alkyl group having 8 to 18 carbon atoms and in which a further group is substituted by an anionic group which imparts water solubility, as for example by a carboxyl, sulfate, or sulfonate group. Preferred amphoteric surfactants are N—($C_{12}$-$C_{18}$)alkyl β-aminopropionates and N—($C_{12}$-$C_{18}$)alkyl β-iminodipropionates in the form of alkali metal and mono-, di-, and trialkylammonium salts. Suitable further surfactants are also amine oxides. These are oxides of tertiary amines having a long-chain group of 8 to 18 carbon atoms and two usually short-chain alkyl groups having 1 to 4 carbon atoms. Preference is given here, for example, to the $C_{10}$ to $C_{18}$ alkyldimethylamine oxides, fatty acid amidoalkyl-dimethylamine oxide.

The amount of the amphoteric surfactants in the compositions of the invention may be up to 10 wt %, based on the overall weight of the completed compositions.

Refatting agents (E) used may be preferably lanolin and lecithin, unethoxylated and polyethoxylated or acylated lanolin derivatives and lecithin derivatives, polyol fatty acid esters, mono-, di-, and triglycerides such as glyceryl oleate or PEG-7 glyceryl cocoate, for example, and/or fatty acid alkanolamides, the latter serving simultaneously as foam stabilizers. They are used preferably in amounts of 0.01 to 10.0 wt %, more preferably of 0.1 to 5.0 wt %, and especially preferably of 0.5 to 3.0 wt %.

Auxiliaries and adjuvants (g) are, for example, preservatives, fragrances, and dyes.

Suitable preservatives are the preservatives listed in the relevant annex of the European cosmetics legislation, for example phenoxyethanol, benzyl alcohol, parabens, benzoic acid, and sorbic acid; a particularly suitable example is 1,3-bis(hydroxymethyl)-5,5-dimethylimidazolidine-2,4-dione (Nipaguard® DMDMH).

The amount of the preservatives in the compositions of the invention is generally from 0.1% to 2.0 wt %, based on the total weight of the complete compositions.

Fragrances used may be individual odorant compounds, examples being the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexyl-propionate, styrallyl propionate, and benzyl salicylate. The ethers include, for example, benzyl ethyl ethers, the aldehydes include, for example, the linear alkanals having 8 to 18 carbon atoms, citral, citronellal, citronellyloxyacetaldehyde, hydroxycitronellal, lilial, and bourgeonal, the ketones include, for example, the ionones, alpha-isomethylionone and methyl cedryl ketone, the alcohols include anethole, citronellol, eugenol, geraniol, linalool, phenylethyl alcohol, and terpineol, and the hydrocarbons include primarily the terpenes and balsams. Preference is given to using mixtures of different odorants which together produce a pleasing scent note.

Fragrances used may also be natural odorant mixtures, as obtainable from vegetable or animal sources, e.g., pine oil, citrus oil, jasmine oil, lily oil, rose oil, or ylang-ylang oil. Essential oils of relatively low volatility, which are usually used as aromatic components, are also suitable as perfume oils, e.g., sage oil, chamomile oil, clove oil, melissa oil, mint oil, cinnamon leaf oil, linden blossom oil, juniperberry oil, vetiver oil, olibanum oil, galbanum oil, and ladanum oil.

The amount of the fragrances in the compositions of the invention is generally from 0 to 2 wt %, based on the total weight of the completed compositions.

The dyes and color pigments present in the compositions of the invention, both organic and inorganic dyes, may be selected from the corresponding positive list in the Cosmetics Regulation, or the EC list of cosmetic colorants. Also used advantageously are pearlescent pigments, for example pearl essence (guanine/hypoxanthine mixed crystals from fish scales) and nacre (ground bivalve shells), monocrystalline pearlescent pigments, for example bismuth oxychloride (BiOCl), layer-substrate pigments, for example mica/metal oxide, silver-white pearlescent pigments composed of $TiO_2$, interference pigments ($TiO_2$, different layer thickness), color luster pigments ($Fe_2O_3$), and combination pigments ($TiO_2/Fe_2O_3$, $TiO_2/Cr_2O_3$, $TiO_2/$Prussian blue, $TiO_2/$carmine).

The amount of the dyes and pigments in the compositions of the invention is generally from 0.01 to 1.0 wt %, based on the total weight of the completed compositions.

Another subject of the invention is a hairwash composition comprising
(a) one or more N-methyl-N-acylglucamines (I) containing at least 8 wt %, based on the total amount of N-alkyl-N-acylglucamines (I), of compounds having a saturated $C_{16}$, $C_{18}$, or singly or multiply unsaturated $C_{18}$ fatty acid radical Ra—CO—, as component (A),
(b) one or more anionic surfactants from the group of the alkyl ether sulfates and alkyl sulfates, as component (B),
(c) optionally betaine surfactants as component (C),
(d) optionally further surfactants as component (D),
(e) one or more refatting agents as component (E),
(f) water as component (F), and
(g) optionally further additives, such as preservatives, fragrances, and dyes, as component (G), the hairwash composition preferably containing no cationic polymers.

Preferred components a), b), c), d), e), g) correspond to those stated above.

Generally speaking, the hairwash compositions comprise
(a) 0.1 to 10.0 wt %, preferably 1 to 5 wt %, of component (A),
(b) 0.1 to 15 wt %, preferably 1 to 10 wt %, of component (B),
(c) 0 to 10 wt %, preferably 1 to 8 wt %, of component (C),
(d) 0 to 10 wt %, preferably 1 to 6 wt %, of component (D),
(e) 0.01 to 10 wt %, preferably 0.2 to 3 wt %, of component (E),
(f) 45 to 99.8 wt %, preferably 75 to 95 wt %, of component (F),
(g) 0 to 10 wt %, preferably 0.1 to 5 wt %, of component (G).

The hairwash compositions of the invention preferably comprise the above-described alkyl sulfates and/or alkyl ether sulfates and betaine surfactants.

Hairwash compositions in the sense of the invention are shampoos, including haircare shampoos, these being shampoos which as well as a hair-cleansing activity also have a haircare activity. A haircare activity lies in particular in improving ease of combing, shine, and structure of the hair (hair sensation). The surfactant systems used in accordance with the invention are suitable for use in a very wide variety of hairwash compositions, as for example for greasy hair, dry hair, stressed hair, and hair affected by dandruff, in color shampoos, baby shampoos, and sports shampoos.

The invention is illustrated in detail by the examples which follow, without any consequent restriction thereon.

EXAMPLES

The N-methyl-N-acylglucamines described in table 1 were prepared according to EP 0 550 637 from the corresponding fatty acid methyl esters and N-methylglucamine in the presence of 1,2-propylene glycol as solvent, and were obtained in solid form comprising active substance and 1,2-propylene glycol (all figures in wt %).

TABLE 1

Preparation examples for N-methyl-N-acylglucamines

| Preparation example | Methyl ester | Triglyceride | Active substance (%) | 1,2-Propylene glycol (%) | Melting point (° C.) |
|---|---|---|---|---|---|
| 1 | C12/14 (C12: 70%, C14 30%) | — | 90 | 10 | 85 |

TABLE 1-continued

Preparation examples for N-methyl-N-acylglucamines

| Preparation example | Methyl ester | Triglyceride | Active substance (%) | 1,2-Propylene glycol (%) | Melting point (° C.) |
|---|---|---|---|---|---|
| 2 | | Coconut oil (C8: 6%; C10: 6%; C12: 48% C14: 20% C16: 10%; C18: 2%, C18' = 8%) | 90 | 10 | 50 |
| 3 | C16/18 (C16: 60%; C18: 40%) | — | 80 | 20 | 65 |
| 4 | C12/18 unsaturated (C12: 60%, C14: 26%, C16: 4% C18: 1% C18' (oleic acid): 8% C18" = 1% | — | 90 | 10 | 70 |
| 5 | C16/18 unsaturated C16: 32% C18: 8% C18' = 52% C18" = 8% | — | 80 | 20 | 45 |

Aqueous surfactant systems comprising sodium lauryl ether sulfate (SLES) [degree of ethoxylation 2 EO] (Genapol® LRO Liq., Clariant), cocoamidopropylbetaine (Genagen® CAB 818, Clariant), and sugar surfactants, in the mass ratios according to the table below, were produced and adapted to a uniform viscosity of 5000 mPas by addition of sodium chloride. The pH was adjusted to 5.5. The total surfactant content in each case was 15%.

The resulting surfactant systems were subjected to sensory evaluation in hairwash tests (−=poor; o=moderate; +=good).

TABLE 2

Examples of inventive uses/hairwash compositions

| Example | Composition | Ratio | Hair sensation, dry | Ease of hair combing |
|---|---|---|---|---|
| Comparative example 1 | SLES/betaines | 7:3 | − dried out | − |
| Comparative example 2 | SLES/betaine/preparation example 1 | 6:3:1 | − dried out | − |
| Inventive example 1 | SLES/betaine/preparation example 2 | 6:3:1 | + refatting | + |
| Inventive example 2 | SLES/betaine/preparation example 4 | 6:3:1 | + refatting | + |
| Inventive example 3 | SLES/betaine/preparation example 3 | 6:3:1 | + refatting | + |
| Comparative example 3 | SLES/betaine/coco-glucosides | 6:3:1 | − dried out | − |

As is apparent from inventive examples 1-3 and comparative examples 1-3, the glucamides from example 1-3, in contrast to the base system (comparative example 1) and to a glucamide with C12/14 chain fraction (comparative example 2), impart positive sensory effects to the hair and lead to improved ease of combing. Comparable sugar surfactants (comparative example 3) likewise do not have this effect.

FORMULATION EXAMPLES

Formulation Example 1

| Care shampoo | |
|---|---|
| Sodium laureth sulfate (2 EO) | 8% |
| Cocoamidopropylbetaine | 3% |
| N-Alkyl-N-acylglucamine as per preparation example 2 | 2% |
| Cocoamide MEA | 0.5% |
| Sodium chloride | 0.5% |
| Fragrance | 0.5% |
| Preservative | q.s. |
| Water | ad 100% |

Formulation Example 2

| Care shampoo | |
|---|---|
| Sodium laureth sulfate (2 EO) | 8% |
| Cocoamidopropylbetaine | 3% |
| N-Alkyl-N-acylglucamine as per preparation example 4 | 2% |
| Cocoamide MEA | 0.5% |
| Sodium chloride | 0.5% |
| Fragrance | 0.5% |
| Polyquaternium-10 | 0.2% |
| Preservative | q.s. |
| Water | ad 100% |

The stated percentages correspond to weight % and are based on the amount of active component.

Use Example

An inventive shampoo formulation B was assessed for fragrance stabilization. This was done by preparing the formulation, adding fragrance, storing it in closed glass bottles for two weeks at 40° C., and then having a panel of three trained assessors evaluate the remaining fragrance intensity in comparison to a comparative formulation A stored at 25° C.

| Formulation | Comparative formulation A Composition (wt %) | Formulation B Composition (wt %) |
|---|---|---|
| Sodium lauryl ether sulfate | 9 | 7.3 |
| Cocoamidopropylbetaine | 3 | 2.75 |
| Glucamide as per preparation example 4 | 0 | 0.92 |
| PEG-40 hydr. castor oil | 0.2 | 0 |
| PEG-200 glyceryl palmate | 0.5 | 0 |
| PEG-7 glyceryl cocoate | 0.5 | 0 |
| Sodium benzoate | 0.2 | 0.2 |
| Sodium salicylate | 0.2 | 0.2 |
| Polyquaternium-7 | 0.2 | 0.2 |
| "Waterlilly" fragrance | 0.5 | 0.5 |
| Glycerol | 0.8 | 0.8 |
| Water | ad 100 | ad 100 |

-continued

| Formulation | Comparative formulation A Composition (wt %) | Formulation B Composition (wt %) |
|---|---|---|
| Evaluation of the odor after two weeks' storage time at 40° C. | Significantly reduced fragrance intensity, head note degraded | Fragrance intensity largely unchanged |

The result of the experiment shows that formulation B, containing no ethoxylates with terminal OH groups such as PEG-40 hydr. castor oil, PEG-200 glyceryl palmate, or PEG-7 glyceryl cocoate, but instead having a glucamide, exhibits a much better fragrance stability on hot storage. It can therefore be concluded that the use of glucamides rather than of ethoxylates having terminal OH groups, as a hair-conditioning component, solubilizer, or thickener, leads at the same time to an improvement in the fragrance stability.

What is claimed is:

1. A method for conditioning hair, comprising the step of contacting the hair with a hairwash composition comprising at least one N-alkyl-N-acylglucamine of the formula (I) and at least one aqueous surfactant system, wherein the at least one aqueous surfactant system comprises at least one alkyl sulfate and/or one alkyl ether sulfate as anionic surfactant,

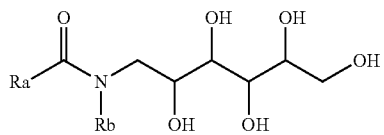

where in the formula (I)
Ra is a linear saturated $C_5$-$C_{21}$ alkyl radical, a branched saturated $C_5$-$C_{21}$ alkyl radical, a linear unsaturated $C_5$-$C_{21}$ alkyl radical, or a branched unsaturated $C_5$-$C_{21}$ alkyl radical and
Rb is a $C_1$-$C_4$ alkyl radical,
and wherein the at least one N-alkyl-N-acylglucamine according to formula (I) comprises at least 8 wt %, based on the total amount of the at least one N-alkyl-N-acylglucamine, of a saturated $C_{16}$, $C_{18}$, or singly or multiply unsaturated $C_{18}$ fatty acid radical Ra—CO—.

2. The method as claimed in claim 1, wherein Rb is a methyl radical.

3. The method as claimed in claim 1, wherein the radical Ra is derived from lauric acid, palmitic acid, stearic acid, oleic acid, linoleic acid, or linolenic acid.

4. The method as claimed in claim 1, wherein the at least one N-alkyl-N-acylglucamine according to formula (I) comprises at least 8 wt % of an unsaturated $C_{18}$ fatty acid radical.

5. The method as claimed in claim 1, wherein the at least one N-alkyl-N-acylglucamine according to formula (I) comprises at least 8 wt % of an unsaturated $C_{18}$ fatty acid radical and at least 30 wt % of a saturated $C_{12}$ fatty acid radical.

6. The method as claimed in claim 1, wherein the aqueous surfactant system comprises an alkyl sulfate and/or an alkyl ether sulfate as anionic surfactant and a betaine surfactant.

7. The method as claimed in claim 1, wherein the aqueous surfactant system comprises a linear $C_8$-$C_{20}$ alkyl sulfate and/or a linear $C_8$-$C_{20}$ alkyl ether sulfate.

8. The method as claimed in claim 7, wherein the aqueous surfactant system comprises lauryl sulfate and/or a lauryl ether sulfate.

9. The method as claimed in claim 1, wherein the aqueous surfactant system comprises an acylamidopropylbetaine or an alkylbetaine.

10. The method as claimed in claim 1, for improving the ease of hair combing.

11. A hairwash composition comprising
(a) at least one N-methyl-N-acylglucamine of the formula (I) containing at least 8 wt %, based on the total amount of N-alkyl-N-acylglucamine, of a saturated $C_{16}$, $C_{18}$, or singly or multiply unsaturated $C_{18}$ fatty acid radical Ra—CO—, as component (A),

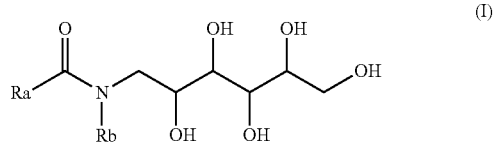

where in the formula (I)
Ra is a linear saturated $C_5$-$C_{21}$ alkyl radical, a branched saturated $C_5$-$C_{21}$ alkyl radical, a linear unsaturated $C_5$-$C_{21}$ alkyl radical, or a branched unsaturated $C_5$-$C_{21}$ alkyl radical and
Rb is a $C_1$-$C_4$ alkyl radical,
(b) at least one anionic surfactant selected from the group consisting of the alkyl ether sulfates and alkyl sulfates, as component (B),
(c) optionally betaine surfactants as component (C),
(d) optionally further surfactants as component (D),
(e) refatting agents as component (E),
(f) water as component (F), and
(g) optionally further additives, such as preservatives, fragrances, and dyes, as component (G).

12. The hairwash composition as claimed in claim 11, with the proviso that the hairwash composition contains no cationic polymers.

13. The hairwash composition as claimed in claim 11 in the form of a greasy hair, dry hair, stressed hair, or dandruff-affected hair hairwash composition, or of a color shampoo, baby shampoo, or sports shampoo.

14. The hairwash composition as claimed in claim 11, wherein Rb is a methyl radical.

15. The hairwash composition as claimed in claim 11, wherein the radical Ra is derived from lauric acid, palmitic acid, stearic acid, oleic acid, linoleic acid, or linolenic acid.

16. The hairwash composition as claimed in claim 11, wherein the at least one N-alkyl-N-acylglucamine according to formula (I) comprises at least 8 wt % of an unsaturated $C_{18}$ fatty acid radical.

17. The hairwash composition as claimed in claim 11, wherein the at least one N-alkyl-N-acylglucamine according to formula (I) comprises at least 8 wt % of an unsaturated $C_{18}$ fatty acid radical and at least 30 wt % of a saturated $C_{12}$ fatty acid radical.

* * * * *